United States Patent [19]

Neumaier

[11] Patent Number: 4,536,351
[45] Date of Patent: Aug. 20, 1985

[54] PROCESS FOR MAKING ARYLDICHLOROPHOSPHANES

[75] Inventor: Hubert Neumaier, Brühl, Fed. Rep. of Germany

[73] Assignee: Hoechst Aktiengesellschaft, Fed. Rep. of Germany

[21] Appl. No.: 561,807

[22] Filed: Dec. 15, 1983

[30] Foreign Application Priority Data

Dec. 29, 1982 [DE] Fed. Rep. of Germany ....... 3248483

[51] Int. Cl.³ .............................................. C07F 9/52
[52] U.S. Cl. .................................................. 260/543 P
[58] Field of Search ..................................... 260/543 P

[56] References Cited

U.S. PATENT DOCUMENTS

| | | | |
|---|---|---|---|
| 2,276,492 | 3/1942 | Jolly et al. | 260/543 P |
| 3,582,293 | 6/1971 | Odenweller | 260/543 P |
| 3,584,043 | 6/1971 | Maier | 260/543 P |
| 3,829,479 | 8/1974 | Kent et al. | 260/543 P |

OTHER PUBLICATIONS

Houben-Weyl, *Methoden der Organischen Chemie*, 4th Ed., vol. XII/1, ("Organic Phosphorus Compounds", Part 1), Gerog Thieme Verlag, Stuttgart, 1963, pp. 294 and 318.

*Primary Examiner*—Natalie Trousof
*Assistant Examiner*—L. Hendriksen
*Attorney, Agent, or Firm*—Connolly and Hutz

[57] ABSTRACT

The disclosure relates to a process for making aryldichlorophosphanes of the general formula

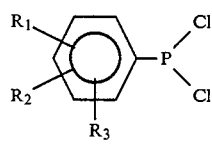

in which $R_1$, $R_2$ and $R_3$ being identical or different each stand for a hydrogen atom, an alkyl group having from 1 to 8 carbon atoms, a halogen atom, an aryl group of an aryloxy group by reacting an arene of the general formula

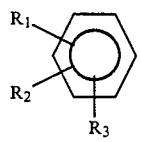

in which $R_1$, $R_2$ and $R_3$ have the meanings given above, with at least 4 mols phosphorus (III) chloride per mol arene in the presence of aluminum chloride, boiling the mixture over a period of several hours and subsequently precipitating the aluminum chloride by adding a complexing agent, filtering and distillatively working up the filtrate. More particularly, the disclosure provides for 0.05 to 0.9 mol aluminum chloride to be used per mol arene and for 1–3 mols finely ground alkali metal chloride to be used as the complexing agent per mol aluminum chloride.

5 Claims, 1 Drawing Figure

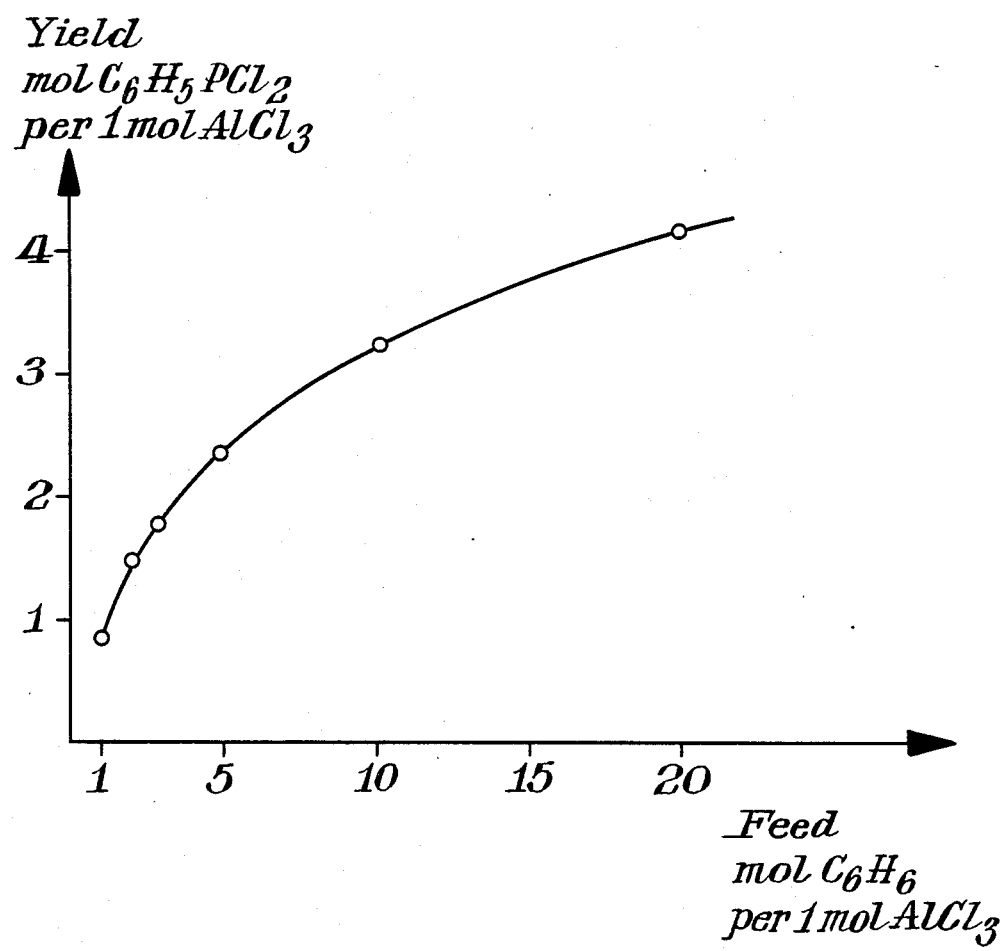

PROCESS FOR MAKING ARYLDICHLOROPHOSPHANES

Acryldichlorophosphanes are important commercial intermediates for the production of organophosphorus compounds which find use e.g. as insecticides, antioxidants, catalysts and stabilizers.

It is known from Houben-Weyl, Methoden der Organischen Chemie, 4th edition, volume XII/1, pages 313–316, that aryl compounds can be reacted under mild conditions with an excess of phosphorus(III)chloride at the boiling point of this latter in the presence of anhydrous aluminum chloride, aryldichlorophosphane being subsequently liberated from the aryldichlorophosphane/aluminum chloride-complex. This method is not limited to the production of phenyldichlorophosphane but can also be used for making nuclear-substituted aryldichlorophosphanes. In accordance with the prior art, it is necessary for at least one mol aluminum chloride to be used per mol aryl compound because of the formation initially of an aryldichlorophosphane/aluminum chloride-complex (equation A)

$$RH + PCl_3 + AlCl_3 \xrightarrow{-HCl} RPCl_2 \cdot AlCl_3 \quad (A)$$

which, after the reaction has been terminated, is split by means of phosphorus oxychloride with the resulting formation of a crystalline phosphorus oxychloride/aluminum chloride-complex (equation B)

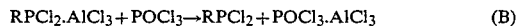

$$RPCl_2 \cdot AlCl_3 + POCl_3 \rightarrow RPCl_2 + POCl_3 \cdot AlCl_3 \quad (B)$$

After filtration, the filtrate is distillatively worked up as usual and aryldichlorophosphane is obtained.

It is also possible for this complex to be split using pyridine or acetic acid ester which can be substituted for phosphorus oxychloride.

An adverse effect of this process resides in the formation of a rather important quantity of by-product (equation B) which originates from the aluminum chloride and substance used for complexing it. As taught by F. M. Kharasova et al., Zh. Obshch. Khim. 37, 902 (167), 86 g phenyldichlorophosphane (this corresponds to a yield of 80%, based on benzene) is obtained together with 230 g by-product which is in the form of the phosphorus oxychloride/aluminum chloride-complex with $AlCl_3$ in excess; in other words, about 2.7 kg by-product is obtained per kg phenyldichloro-phosphane. This by-product can be disposed of either by first hydrolyzing and neutralizing it and then delivering it into waste water, or it can be deposited in solid form. In either case, the by-product is highly pollutive.

It is therefore highly desirable to have a process for making aryldichlorophosphanes permitting the formation of by-products to be considerably reduced.

The present invention now provides a process for making aryl-dichlorophosphanes of the general formula

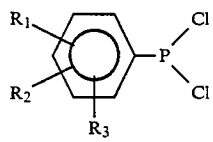

in which $R_1$, $R_2$ and $R_3$ being identical or different each stand for a hydrogen atom, an alkyl group having from 1 to 8 carbon atoms, a halogen atom, an aryl group or an aryloxy group by reacting an arene of the general formula

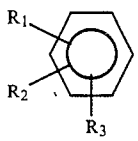

in which $R_1$, $R_2$ and $R_3$ have the meanings given above, with at least 4 mols phosphorus(III)chloride per mol arene in the presence of aluminum chloride, boiling the mixture over a period of several hours and subsequently precipitating the aluminum chloride by adding a complexing agent, filtering and distillatively working up the filtrate, which comprises: using 0.05 to 0.9 mol aluminum chloride per mol arene and 1–3 mols finely ground alkali metal chloride as the complexing agent per mol aluminum chloride.

Sodium or potassium chloride should preferably be used as alkali metal chloride.

The finely ground alkali metal chloride should conveniently be used in the form of particles with a size of less than 0.25 mm, preferably less than 0.08 mm. It is also good practice to use 0.05 to 0.7 mol $AlCl_3$ per mol arene and 1.1 to 2.0 mol NaCl or KCl per mol $AlCl_3$.

The arenes should preferably be selected from benzene, mono- or polyalkylated benzenes with alkyl groups having 1 to 5 carbon atoms, e.g. toluene, ethylbenzene, xylenes, mono- or polyhalogenated benzenes, e.g. fluorobenzene, chlorobenzene, bromobenzene, dichlorobenzenes or dihalogenobenzenes having different halogen atoms, such as chlorofluorobenzene, or an arylated benzene, e.g. biphenyl.

It has unexpectedly been found that very good yields, generally significantly more than 1 mol aryldichlorophosphane per mol aluminum chloride used are obtained. Shown in the diagram attached hereto are the yields in mol/mol aluminum chloride obtained with the use of different benzene/aluminum chloride-molar ratios in the production of phenyl-dichlorophosphane.

This result could not be foreseen as theoretically at most 1 mol phenyldichlorophosphane per mol aluminum chloride would have been expected to be obtained in accordance with the prior art, due to formation of the phenyldichlorophosphane/aluminum chloride-complex, $C_6H_5PCl_2 \cdot AlCl_3$, cf. equation A.

In the process of this invention, 4 up to preferably 12 mols phosphorus(III)chloride are used per mol arene, the excess serving as solvent. As a result of the high excess, less by-products are obtained during the reaction and the subsequent precipitation of aluminum chloride in the form of an alkali metal tetrachloroaluminate-complex is rendered easier.

In the process of this invention, the aluminum chloride present after the reaction in the form of an aryldichlorophosphane/aluminum chloride-complex is precipitated from the reaction solution with the aid of finely ground alkali metal chloride in the form of an alkali metal tetrachloroaluminate. Use is more particularly made of ground alkali metal chloride passing through a sieve with meshes 0.25 mm, preferably 0.08 mm wide.

The steps described enable the quantity of by-product obtained heretofore to be considerably reduced per unit weight aryldichlorophosphane. As a result, less expenses firstly for feed material and secondly for by-product deposition are incurred, and problems relating to environmental protection are beneficially influenced.

The process of this invention can more particularly be carried out as follows: arene, phosphorus(III)chloride, and aluminum chloride are boiled under reflux over a period of several hours in a reactor provided with a stirrer and reflux condenser, the aluminum chloride becoming dissolved. The boiling temperature determined to a far-reaching extent by the excess of phosphorus(III)chloride lies at 74°–76° C. Hydrogen chloride formed during the reaction can be introduced into a scrubbing tower series-connected to the reactor. The reaction period depends on the reactivity of the arene used and should preferably vary within 4 to 12 hours. Shorter reaction periods result in lower yields while longer reaction periods promote the formation of undistillable by-products. After the reaction has been terminated, it is possible for the necessary quantity of ground alkali metal chloride to be added either portionwise in powder form or continuously by means of a dosing screw or in the form of a suspension in phosphorus(III)chloride within 15 to 30 minutes into the mixture boiling under reflux. This causes alkali metal tetrachloroaluminate to precipitate as a crystalline well filterable product. After a post-reaction period of 0.5 to 1 hour, the whole is cooled to 20°–25° C. and alkali metal tetrachloroaluminate is separated together with alkali metal chloride in excess by means of a suction filter, preferably with the aid of a centrifuge, and washed with phosphorus(III)chloride. Phosphorus(III)chloride and arene are distillatively separated as usual from the filtrates. After replacement of the quantities consumed, the two materials so separated are used in a fresh batch to ensure high yields, based on these two reactants. Pure aryldichlorophosphane is obtained by subjecting the distillation residue to distillation under vacuum.

The following Examples illustrate the invention.

EXAMPLE 1

(Comparative Example)

8800 g (64 mols) phosphorus(III)chloride, 780 g (10 mols) benzene and 1361 g (10 mols) anhydrous aluminum chloride of 98% strength were boiled for 5 hours under reflux in a reactor provided with a stirrer and reflux condenser. Next, 1535 g (10 mols) phosphorus oxychloride was added dropwise within 30 minutes. After a post-reaction period of 30 minutes, the whole was cooled to 25° C., the formed aluminum chloride/phosphorus oxychloride-complex was filtered off and washed with phosphorus(III)chloride. 3128 g crystalline matter moist with $PCl_3$ was obtained (theoretically: 1535 g $POCl_3 + 1361$ g $AlCl_3 = 2896$ g). Phosphorus(III)chloride in excess and unreacted benzene were expelled from the filtrate under atmospheric pressure and the residue was distilled under vacuum. 1561 g phenyldichlorophosphane (bp: 95° C. at 25 millibars) was obtained. Yield: 0.87 mol $C_6H_5PCl_2$ per mol $AlCl_3$.

EXAMPLE 2

8800 g (64 mols) phosphorus(III)chloride, 780 g (10 mols) benzene and 680 g (5 mols) anhydrous aluminum chloride of 98% strength were boiled for 5 hours under reflux (75° C.) in a reactor provided with a stirrer and reflux condenser. Before the end of the reaction period, 1 liter condensate was taken from the base of the reflux condenser by means of a suitable device and 497 g (8.5 mols) finely ground sodium chloride consisting of particles with a size of less than 0.08 mm was suspended therein while stirring. Next, the suspension was metered within 30 minutes into the boiling reaction mixture, sodium tetrachloroaluminate being precipitated as a crystalline well filterable product. The whole was stirred for a further 30 minutes under reflux, 1 liter condensate was taken from the reflux condenser and kept ready for use as washing liquid in the next operation. After cooling the reaction mixture to 20°–25° C., the salt mixture was separated by means of a continuous bulk centrifuge and washed with the condensate kept ready. 1225 g salt mixture (moist with $PCl_3$) (theoretically: 680 g $AlCl_3 + 497$ g $NaCl = 1177$ g) was obtained. Phosphorus(III)chloride in excess and unreacted benzene were distillatively separated from the filtrate at atmospheric pressure and, after replacement of the quantities consumed, used in the next bath. The remaining crude product was distilled under vacuum and 1250 g pure phenyldichlorophosphane was obtained (bp: 95° C. at 25 millibars). Yield: 1.4 mols $C_6H_5PCl_2$ per mol $AlCl_3$.

EXAMPLES 3 TO 6

The procedure was as in Example 2 but varying proportions of phosphorus(III)chloride, benzene, aluminum chloride and sodium chloride were used. The quantities used and yields obtained are indicated in the Table hereinafter which also shows the values determined for Example 2 and Comparative Example 1.

EXAMPLE 7

(Comparative Example)

112.5 g (1 mol) chlorobenzene, 1100 g (8 mols) phosphorus(III)chloride and 136.2 g (1 mol) aluminum chloride of 98% strength were heated for 12 hours under reflux. Next, 87.8 g (1.5 mols) sodium chloride (particles with a size smaller than 0.08 mm) suspension in 200 milliliters phosphorus(III)chloride was added dropwise and the reaction mixture was heated for 30 minutes under reflux. The whole was allowed to cool to 20° C., filtered and the filtrate was worked up as described in Example 2.

153.7 g chlorophenyldichlorophosphane which was in the form of an isomer mixture was obtained at 85°–88° C. under a pressure of 1.3 millibars. Yield: 0.72 mol $ClC_6H_4$—$PCl_2$ per mol $AlCl_3$.

EXAMPLE 8

The procedure was as in Example 7 but only 68.1 g (0.5 mol) aluminum chloride of 98% strength and 44 g (0.75 mol) sodium chloride were used.

110 g chlorophenyldichlorophosphane which was in the form of an isomer mixture was obtained. ($^{31}$P-NMR: 91.3% para; 1.3% meta; 7.4% ortho). Yield: 1.03 mols $ClC_6H_4$—$PCl_2$ per mol $AlCl_3$.

EXAMPLE 9

(Comparative Example)

92.1 g (1 mol) toluene, 1100 g (8 mols) phosphorus(III)chloride and 136.2 g (1 mol) aluminum chloride of 98% strength were heated for 4 hours under reflux. Next, 87.8 g (1.5 mols) sodium chloride (particles with a size smaller than 0.08 mm) suspension in 200 ml phosphorus(III)chloride was added dropwise and the reaction mixture was heated for 30 minutes under reflux. After cooling to 20° C., the whole was filtered and the filtrate was worked up as described in Example 2.

153 g toluyldichlorophosphane which was an isomer mixture was obtained at 88°–91° C. under 2.7 millibars. Yield: 0.79 mol $CH_3C_6H_4$—$PCl_2$ per mol $AlCl_3$.

EXAMPLE 10

The procedure was as in Example 9 but only 68.1 g (0.5 mol) aluminum chloride of 98% strength and 44 g (0.75 mol) sodium chloride were used.

115.8 g toluyldichlorophosphane which was an isomer mixture was obtained ($^{31}$P-NMR: 59.2% para; 37.4% meta; 3.4% ortho). Yield: 1.2 mols $CH_3C_6H_4$—$PCl_2$ per mol $AlCl_3$.

TABLE

| | Quantities used | | | | | | | | Molar ratio $C_6H_4$:$AlCl_3$ | Molar ratio |
|---|---|---|---|---|---|---|---|---|---|---|
| | $PCl_3$ | | $C_6H_6$ | | $AlCl_3$ (98%) | | | | | |
| Example | (g) | (mol) | (g) | (mol) | (g) | (mol) | (g) | (mol) | | |
| | | | | | | | NaCl | | | NaCl:$AlCl_3$ |
| 2 | 8800 | 64 | 780 | 10 | 680 | 5 | 497 | 8.5 | 2:1 | 1.7 |
| 3 | 11000 | 80 | 1170 | 15 | 680 | 5 | 497 | 8.5 | 3:1 | 1.7 |
| 4 | 11000 | 80 | 1560 | 20 | 545 | 4 | 351 | 6 | 5:1 | 1.5 |
| 5 | 11000 | 80 | 1560 | 20 | 272 | 2 | 175 | 3 | 10:1 | 1.5 |
| 6 | 11000 | 80 | 1560 | 20 | 136 | 1 | 70 | 1.2 | 20:1 | 1.2 |
| | | | | | | | $POCl_3$ | | | $C_6H_6$:$POCl_3$ |
| 1 comparative Example | 8800 | 64 | 780 | 10 | 1361 | 10 | 1535 | 10 | 1:1 | 1.0 |

TABLE

| | Yield $C_6H_5PCl_2$ | | | | Quantity (g) $AlCl_3$ + NaCl per 100 g $C_6H_5PCl_2$ |
|---|---|---|---|---|---|
| Example | (g) | (mol) | g per g $AlCl_3$ | mol per mol $AlCl_3$ | |
| 2 | 1250 | 6.98 | 1.83 | 1.40 | 94.16 |
| 3 | 1472 | 8.22 | 2.16 | 1.65 | 81.6 |
| 4 | 1636 | 9.14 | 3.00 | 2.28 | 54.7 |
| 5 | 1138 | 6.35 | 4.18 | 3.18 | 39.3 |
| 6 | 751 | 4.20 | 5.52 | 4.20 | 27.4 |
| | | | | | $AlCl_3$ + $POCl_3$ |
| 1 (comparative Example) | 1561 | 8.72 | 1.15 | 0.87 | 185.5 |

We claim:

1. In a process for making aryl-dichlorophosphanes of the formula

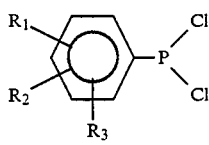

in which $R_1$, $R_2$ and $R_3$ being identical or different each stand for a hydrogen atom, an alkyl group having from 1 to 8 carbon atoms, a halogen atom, an aryl group or an aryloxy group by reacting an arene of the formula

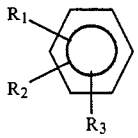

in which $R_1$, $R_2$ and $R_3$ have the meanings given above, with excess phosphorus(III)chloride in the presence of aluminum chloride by boiling the mixture over a period of several hours and subsequently precipitating the aluminum chloride by adding a complexing agent, filtering and distillatively working up the filtrate, the improvement which comprises: using 0.05 to 0.9 mol aluminum chloride per mol arene and 1–3 mols finely ground alkali metal chloride as the complexing agent per mol aluminum chloride.

2. A process for making an aryl-dichlorophosphane of the formula

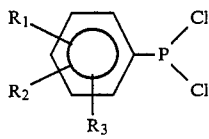

in which $R_1$, $R_2$ and $R_3$, being identical or different, each stand for a hydrogen atom, an alkyl group having from 1 to 8 carbon atoms, a halogen atom, an aryl group or an aryloxy group, said process comprising: reacting an arene of the formula

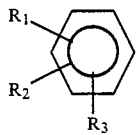

in which $R_1$, $R_2$ and $R_3$ have the meanings given above, with at least 4 moles phosphorus(III)chloride per mole arene, in the presence of 0.05 to 0.9 mol aluminum chloride per mole arene, subsequently, precipitating the aluminum chloride by adding, as a complexing agent therefor, 1–3 mols finely ground alkali metal chloride per mol aluminum chloride, and recovering the aryl-dichlorophosphane from the filtrate.

3. The process according to claim 2, wherein:

a reaction mixture comprising the arene, the aluminum chloride and the phosphorus(III)chloride is boiled for several hours;

the finely ground alkali metal chloride is then added, resulting in precipitation of a crystalline, filterable alkali metal tetrachloroaluminate byproduct;

said byproduct, moist with phosphorus(III)chloride, is separated from the aryl dichlorophosphorane product, excess phosphorus(III)chloride, and unreacted arene, and the aryl dichlorophosphorane product is recovered by distillatively separating therefrom the excess phosphorus(III)chloride and unreacted arene.

4. The process according to claim 2 wherein 0.05 to 0.7 mol $AlCl_3$ is used per mole arene.

5. The process according to claim 2 wherein the amount of phosphorus(III)chloride used is 4–12 moles per mole arene.

* * * * *